(12) United States Patent
Shelley et al.

(10) Patent No.: US 6,956,228 B2
(45) Date of Patent: Oct. 18, 2005

(54) SURFACE CLEANLINESS MEASUREMENT WITH INFRARED SPECTROSCOPY

(75) Inventors: Paul H. Shelley, Lakewood, WA (US); Bruce R. Davis, Seattle, WA (US)

(73) Assignee: The Boeing Company, Chicago, IL (US)

( * ) Notice: Subject to any disclaimer, the term of this patent is extended or adjusted under 35 U.S.C. 154(b) by 392 days.

(21) Appl. No.: 10/329,734

(22) Filed: Dec. 26, 2002

(65) Prior Publication Data

US 2003/0232448 A1 Dec. 18, 2003

Related U.S. Application Data

(63) Continuation-in-part of application No. 10/171,579, filed on Jun. 13, 2002, now Pat. No. 6,784,431, and a continuation-in-part of application No. 10/171,870, filed on Jun. 13, 2002, now Pat. No. 6,797,958, and a continuation-in-part of application No. 10/171,872, filed on Jun. 13, 2002, now Pat. No. 6,794,651.

(51) Int. Cl.[7] .............................................. G01N 21/86
(52) U.S. Cl. ................................... 250/559.4; 250/574
(58) Field of Search .............................. 250/559.4, 574, 250/221, 341.8, 341.1, 338.1; 356/237.4, 239.7, 234

(56) References Cited

U.S. PATENT DOCUMENTS

| | | |
|---|---|---|
| 4,657,390 A | 4/1987 | Doyle |
| 4,791,296 A | 12/1988 | Carpio |
| 4,800,279 A | 1/1989 | Hieftje et al. |
| 5,015,856 A | 5/1991 | Gold |
| 5,381,228 A | 1/1995 | Brace |
| 5,714,758 A | 2/1998 | Neu |
| 5,952,660 A | 9/1999 | Kip et al. |
| 6,788,405 B2 * | 9/2004 | Hunt ........................ 356/237.4 |

FOREIGN PATENT DOCUMENTS

| | | |
|---|---|---|
| DE | 100 10 839 A | 9/2001 |
| GB | 1 380 725 A | 1/1975 |

OTHER PUBLICATIONS

Townshend, A. (Ed): "Encyclopedia of Analytical Science, PASSAGE" Encyclopedia of Analytical Science, XX, XX, 1995, pp. 4930–4932, XP002259402 the whole document.

* cited by examiner

*Primary Examiner*—Que T. Le
(74) *Attorney, Agent, or Firm*—Harness Dickey & Pierce P.L.C.

(57) ABSTRACT

A method is provided for determining an amount of a contaminant on a surface. Base values of infrared energy reflected from the surface without the contaminant at first and second wavelengths is determined. The values of infrared energy reflected from the surface with the contaminant at the first and second wavelengths are also determined. The values of infrared energy absorbed by the contaminant on the surface are determined at the first and second wavelengths. A difference of the absorbance at the first and second wavelengths is determined. The difference is correlated to an amount of the contaminant on the surface.

42 Claims, 5 Drawing Sheets

SURFACE CLEANLINESS MEASUREMENT WITH INFRARED SPECTROSCOPY

CROSS-REFERENCE TO RELATED APPLICATIONS

This application is a continuation-in-part of U.S. patent application Ser. Nos. 10/171,579 filed on Jun. 13, 2002, now U.S. Pat No. 6,784,431 by Shelley et al, entitled "Method of Measuring Anodize Coating Amount Using Infrared Absorbance" and assigned to the Assignee of this Application, No. 10/171,870 filed on Jun. 13, 2002, now U.S. Pat. No. 6,797,958 to Shelley et al, and entitled "Method of Measuring Sol-Gel Coating Thickness Using Infrared Absorbance" and assigned to the Assignee of this Application; and No. 10/171,872 filed on Jun. 13, 2002, now U.S. Pat. No. 6,794,651 to Shelley et al, and entitled "Method of Measuring Chromated Conversion Coating Amount Using Infrared Absorbance" and assigned to the Assignee of this Application. The disclosures of the above applications are incorporated herein by reference.

FIELD OF THE INVENTION

The present invention relates generally to measuring and, more specifically, to measuring an amount of a contaminant on a surface with infrared spectroscopy.

BACKGROUND OF THE INVENTION

During the processing of a material, a measurement of a cleanliness (quantity of contaminant) of a surface of the material may be required. For example, when painting, priming, or sealing a surface, verification of an adequate surface cleanliness is useful to ensure adequate adhesion between the paint, primer or sealant and the surface. Regulatory imposed reductions in the amount of solvents that can be used in applying paints, primers and sealants may require that a surface be cleaned to a higher standard than heretofore required. That is, the new regulatory mandated high-solids materials that are used in the painting, priming and sealing operations are more sensitive to surface contaminants than the old high-solvent systems. Because the solvents help clean the surface, the reduction in the amount of solvents that are used require that a cleanliness of the surface being painted, primed or sealed be verified to a lower level (or quantity) of contaminants than has previously been required.

Additionally, the acceptable amount of a contaminant on the surface may be different for different contaminants. That is, the type of contaminant that maybe found on the surface may vary and may have different properties such that the quantity of solvents that are used in the painting, priming, and sealing operations may be able to remove more or less of the specific contaminant. For example, in the commercial aircraft industry, various contaminants can be found on the exterior surface or skin of the aircraft that is to be painted, primed or sealed. Such contaminants include silicone oil, hydrocarbon oil, temporary protective coating (TPC) residue, aqueous cleaners, fluorocarbons, synthetic oils, long chain alcohols, and cutting oils. Silicone oil is a chain of silicon and oxygen atoms with alternating atoms for each element. The silicone oil is typically used as a lubricant or a releasing agent. Hydrocarbon oil is a chain with a carbon atom backbone and either hydrogen or simple side chains from each carbon atom. Hydrocarbon oil has multiple uses such as a lubricant or a fuel. The TPC is a polymeric material of various chemical compositions that is put onto aircraft to protect the aluminum skin during the manufacturing process. Aqueous cleaners are mostly soap and water with various formulations for the soap. These cleaners sometimes have some organic solvent in them as well to make them clean more efficiently. Fluorocarbons are made up primarily of carbon and fluorine atoms with various arrangements and side chains. They are often used as a lubricants and in refrigeration or cooling systems. Synthetic oil is a long chain ester that is typically used as a lubricant. Long chain alcohols are hydrocarbon chains with an alcohol group on one end. Long chain alcohols are drilling lubricants and fastener lubricants. Cutting oils are hydrocarbon lubricants that are often used with an emulsifier so they can be diluted with water to help cool the cutting or drilling process.

If the surface is not cleaned to the required level of cleanliness, the paint, primer or sealant applied to the surface may not properly adhere. The effects of too high of a contaminant level can show up immediately, for example in the form of bubbling and/or blistering, or can show up later, for example in the form of premature failure or wearing of the paint, primer or sealant on the surface. When the surface contaminant causes failure of the paint, primer or sealant, the surface is reworked to remove the defective layer of paint, primer or sealant and to clean the surface to the required level prior to painting, priming or sealing the surface again. Additionally, the new coating will need to be worked into the old coating to provide a desired appearance. The reworking of the surface increases the time spent painting, priming or sealing the surface and increases the cost. The re-work process also generates an additional waste disposal problem in many cases.

Thus, it is desirable to provide a quantitative measure of surface cleanliness prior to performing the painting, priming or sealing operation. Additionally, because the level of a contaminant that is acceptable can differ based upon the particular contaminant, it is also desirable to be able to quantitatively measure a specific contaminant on a surface to be processed.

SUMMARY OF THE INVENTION

The present invention provides a method for quickly and efficiently determining an amount of a contaminant on a surface. The "amount" of contaminant can be provided as a weight of the contaminant. The method may be employed in an in-line production facility or may be used intermittently as desired. The method can be used to provide a quantitative measurement, such as an actual contaminant amount, or used as a go/no-go indicator.

In a first aspect, according to the principles of the present invention, a method of determining an amount of a contaminant on a surface is disclosed. The method includes the steps of: (1) determining a difference of first and second absorbance values of infrared energy absorbed in a contaminant on a surface at respective first and second wavelengths, with the second wavelength being different than the first wavelength, and (2) correlating the difference to an amount of the contaminant on the surface.

In another aspect, according to the principles of the present invention, a different method of determining an amount of a contaminant on a surface is disclosed. The method includes the steps of: (1) transmitting an infrared beam through a contaminant on a surface at a predetermined incident beam angle relative to normal, the transmitted beam having a cross-sectional area to produce a predetermined spot size on the surface; (2) reflecting the infrared beam off the surface to form a reflected beam; (3) detecting the reflected beam; (4) comparing infrared energies $I_{c1}$ and $I_{c2}$ of the reflected beam at respective first and second wavelengths, the first wavelength being different than the second wavelength, with predetermined values of infrared energies $I_{o1}$ and $I_{o2}$ at the respective first and second wavelengths reflected off a standard having a quantity of the contaminant below a predetermined value to determine absorbance values $A_1$ and $A_2$ at the respective first and second wavelengths for the surface having the contaminant; (5) determining a difference of the absorbance values $A_1$ and $A_2$; and (6) correlating the difference to an amount of the contaminant on the surface.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 6A is a graph of infrared absorbance for various quantities of synthetic lube oil using the testing setup of FIG. 1; and FIG. 6B is a graphical illustration of the relation between synthetic lube oil amount and infrared absorbance difference in accordance with the present invention.

DETAILED DESCRIPTION OF THE PREFERRED EMBODIMENT

The following description of the preferred embodiment is merely exemplary in nature and is in no way intended to limit the invention, its application, or uses.

The present invention provides a method for determining an amount, preferably given as contaminant weight, of a contaminant on a surface by correlating a difference of infrared absorbance of the contaminant at two wavelengths $\lambda_1$ and $\lambda_2$ to the contaminant amount.

Figure 1:
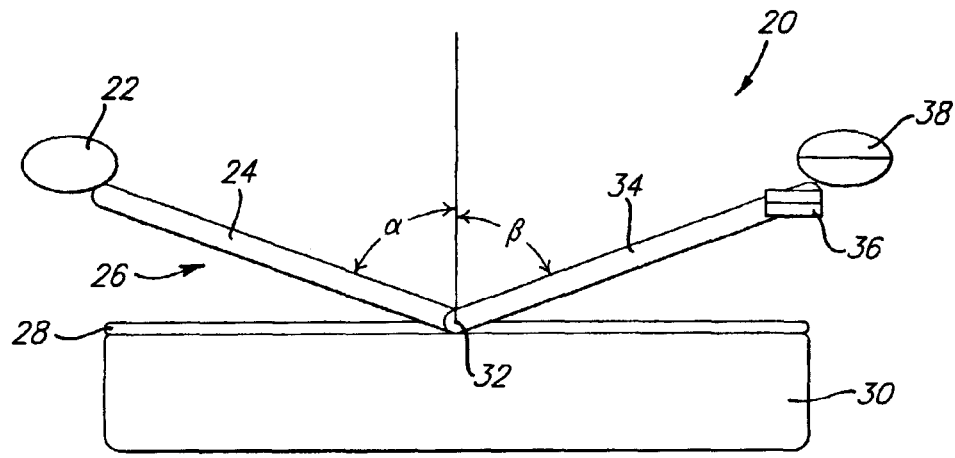
FIG. 1 is a side view of a testing setup according to the principles of the present invention.
Figure 3:
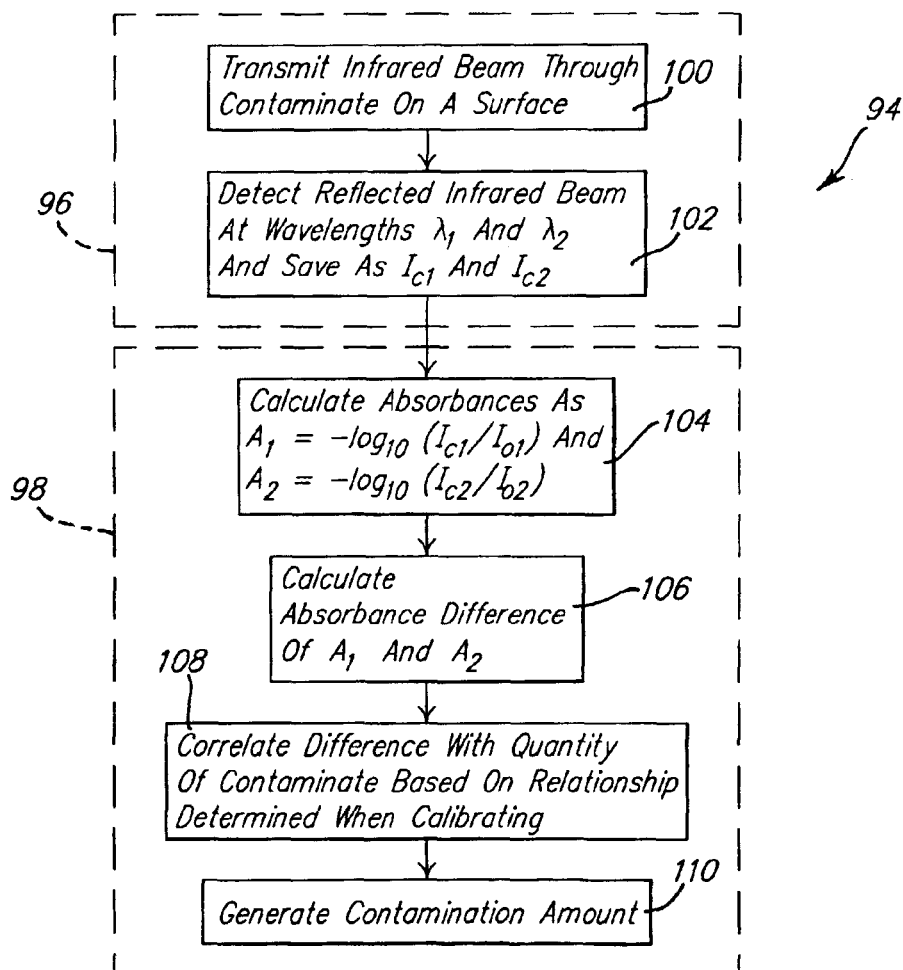
FIG. 3 is a flow chart of the testing process according to the principles of the present invention.
Figure 2:
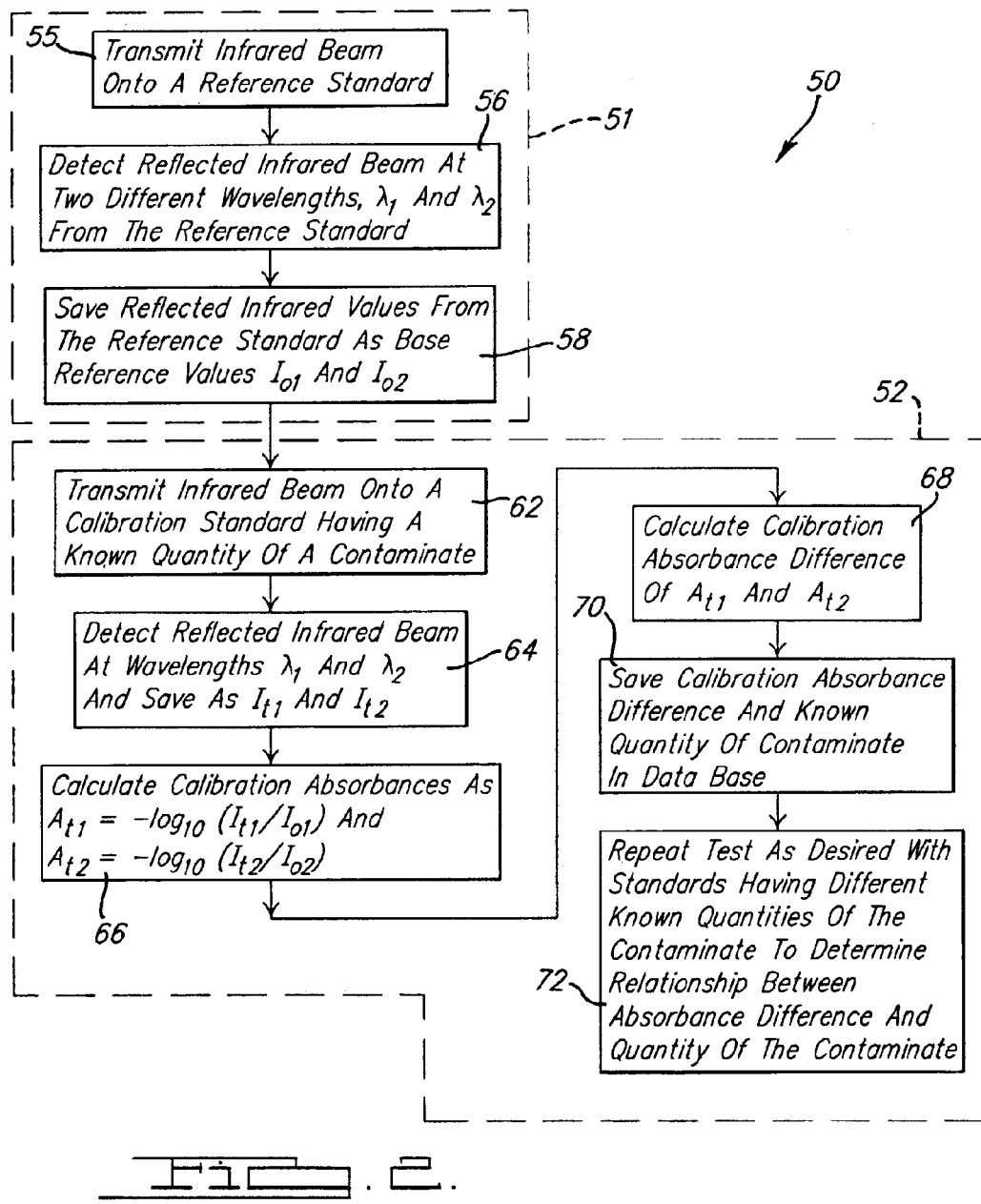
FIG. 2 is a flow chart of the calibration and data gathering of the testing process according to the principles of the present invention.

By way of overview and with reference to FIGS. 1–3, one presently preferred embodiment according to the principles of the present invention determines a quantity of a contaminant (contaminant amount) on a surface using a testing setup 20. Testing setup 20 includes an infrared source 22 that transmits an infrared transmission beam 24 along a predetermined incident beam path 26 through a contaminant layer 28 and onto surface 30 on which contaminant layer 28 resides. Infrared transmission beam 24 is transmitted in such a fashion to form a spot 32 having a predetermined size on contaminant layer 28. infrared transmission beam 24 is reflected off surface 30 to form a reflected beam 34. Reflected beam 34 passes through contaminant layer 28 and through a dual channel filter 36 which filters reflected beam 34 into two predetermined wavelengths $\lambda_1$ and $\lambda_2$. After passing through dual channel filter 36, reflected beam 34 is detected by a dual channel infrared detector 38. Initially, base reference values $I_{o1}$ and $I_{o2}$ of the infrared energy of reflected beam 34 at first and second wavelengths $\lambda_1$ and $\lambda_2$ reflected off a reference standard are determined. Contaminant values $I_{c1}$ and $I_{c2}$ of the Infrared energy of reflected beam 34 at first and second wavelengths $\lambda_1$ and $\lambda_2$ reflected off surface 30 and passing through contaminant layer 28 are determined. Base reference values $I_{o1}$ and $I_{o2}$ and contaminant values $I_{c1}$ and $I_{c2}$ are used to determine absorbance values $A_1$ and $A_2$. A difference of absorbance values $A_1$ and $A_2$ is correlated to a contaminant amount. The specific details of testing setup 20 and the $I_{c2}$, absorbance values $A_1$ and $A_2$ and correlation with contaminant amount are described with more particularity below.

The methods according to the principles of the present invention can be used on a variety of surfaces 30. Surface 30 must be capable of reflecting infrared transmission beam 24 to form reflected beam 34. Surfaces having a refractive index greater than about 3 can utilize the methods of the present invention to determine a quantity of contaminant on the surface. Preferably, surface 30 is a metallic surface having a refractive index greater than about 8, such as, without limitation, aluminum, aluminum alloy, titanium, and titanium alloy. However, the methods of the present invention can be used on other surfaces 30 having a refractive index greater than about 3, as stated above, such as geranium which has a refractive index of about 4. Thus, it should be appreciated that the methods of the present invention can be used on other surfaces without departing from the spirit of the invention.

In a presently preferred embodiment, testing setup 20 is a simple infrared bandpass filter system, including an infrared generator, transmitter, reflection optics, dual bandpass filter, and duel channel detector. A non-limiting example of a simple infrared bandpass filter system is a Coating Weight Reader produced by Personal Instruments. However, it should be appreciated that other infrared systems are employable with this testing setup 20, such as, without limitation, standard broadband infrared spectrometers and infrared imaging systems. Non-limiting examples of standard broadband infrared spectrometers are a Thermo Nicolet 760 FT-IR spectrometer system fitted with a Harrick Refractor® accessory and a Surface Optics Corporation SOC 400 portable FT-IR spectrometer with a grazing angle reflectance attachment. Non-limiting examples of infrared imaging systems employable with the present invention include Image-Max® produced by Thermo Nicolet. It will be appreciated that various infrared systems may be used as an in-line production element or a portable, hand held arrangement.

Infrared transmission beam 24 is suitably transmitted as a broadband mid-infrared light beam (2.5–25 microns typically). In a preferred embodiment, as stated above, reflected beam 34 is suitably filtered by a dual channel filter 34 at preferred wavelengths $\lambda_1$ and $\lambda_2$ that are selected based upon the particular contaminant that is to be measured, as described in more detail below. Dual channel filter 36 may act on either infrared transmission beam 24 or, as shown and as preferred, on reflected beam 34. It will be appreciated, however, that when using either the standard broadband infrared spectrometer or infrared imaging systems, dual channel filter 36 may suitably be replaced by software performing the same function. When detected reflected beam 34 has wavelengths within the disclosed ranges, a substantially linear relationship has been found to exist between a difference of infrared absorbance at the first and second wavelengths $\lambda_1$ and $\lambda_2$ and the contaminant amount, as discussed in more detail below.

Broadband infrared transmission beam 24 is generated by infrared source 22. Infrared source 22 is any acceptable source of infrared energy known in the art that can produce infrared transmission beam 24 having the desired wavelength region. One suitable example of a preferred embodiment of infrared source 22 is the ReflectIR-P1N source made by Ion Optics.

Dual channel infrared detector 38 in the filtered system described here is suitably arranged to detect reflected beam 34. One suitable, non-limiting example of a presently preferred dual channel infrared detector 38 is the Eltec Corp. 406MAY-XXX where XXX indicates the particular dual channel filter 36 that is used with dual channel infrared detector 38.

Infrared transmission beam 24 defines spot 32 on contaminant layer 28. The size of spot 32 is predetermined by use of a mask and/or focusing optics in communication with infrared source 22. In a presently preferred embodiment, the size of spot 32 is preferably within a range of about 2 mm to about 35 mm in diameter. In one embodiment, spot 32 is preferably an oval shape that is about 12.5 mm by about 25 mm. However, a size of spot 32 that is either above or below the preferred range is considered within the scope of this invention.

Incident beam path 26 is directed such that the incident beam angle $\alpha$ is within a desired range. In one presently preferred embodiment, incident beam angle $\alpha$, relative to normal, is preferably about 70° to about 80°. In a particular embodiment, incident beam angle $\alpha$ is preferably about 75°. A reflected beam angle $\beta$, equals the incident beam angle $\alpha$. As a result, reflected beam angle $\beta$ is preferably within a range of about 70° to about 80° from normal. In one presently preferred embodiment, reflected beam angle $\beta$ is preferably about 75°.

It should be appreciated that changes can be made to testing setup 20 without departing from the scope of the invention. For example, a polarizer can be added to the testing setup 20 to improve sensitivity. The polarizer can be added to polarize either infrared transmission beam 24 or reflected beam 34. By polarizing infrared transmission beam 24 or reflected beam 34, sensitivity of testing setup 20 can be improved so that lower levels of contamination can be determined.

Referring now to FIG. 2, a process 50 for preparing testing setup 20 to determine an amount of contaminant on surface 30 is illustrated. This process is substantially the same for an infrared bandpass filter system, standard broadband infrared spectrometer system, and infrared imaging system. Process 50 includes a reference value determining portion, as indicated in block 51, and a calibration data determining portion, as indicated in block 52. The reference value determining portion, as indicated in block 51, obtains base reference values $I_{o1}$ and $I_{o2}$ at the respective first and second wavelengths $\lambda_1$ and $\lambda_2$ for infrared energy reflected by a reference standard. A reference standard is a standard that is representative of the surface 30 that is to be tested and has a level of a particular contaminant below a predetermined quantity which can be considered to be clean or free from the contaminant. Preferably, the reference standard has a contaminant level less than or equal to about 0.01 mg/ft$^2$. This low contaminant level is below the detection limits of most infrared systems and, is considered to be clean. Also preferably, the reference standard has a similar surface finish as that of surface 30 to be tested. For example, a gold mirror that has a contaminant level below the predetermined quantity can be used as a reference standard for typical exterior surfaces of aircraft made from aluminum, aluminum alloy, titanium and titanium alloy. The low level of contaminants for a reference standard is chosen because of the small peaks in infrared absorbance by contaminant layer 28 when using the methods according to the principles of the present invention. That is, the present invention determines small changes in absorbance in reflected beam 34 and, as such, requires reference to a reference standard having a contaminant level of a small magnitude such that a difference in absorbance between a reference standard and a contaminated surface 30 provides useful data. It should be appreciated, however, that the contaminant level on the reference standard can be greater than the preferred amount and/or have a surface finish that is different than the finish of surface 30, and still be within the scope of the present invention.

The first step in determining infrared base reference values $I_{o1}$ and $I_{o2}$ is to transmit infrared transmission beam 24 along incident beam path 26 onto the surface of a reference standard as indicated at block 55. Reflected beam 34 passes through dual channel filter 36 wherein reflected beam 34 is filtered into first and second wavelengths $\lambda_1$ and $\lambda_2$ and detected by the dual channel infrared detector 38, as indicated in block 56. The infrared energies of the filtered reflected beam 34 off the reference standard are saved as base reference values $I_{o1}$ and $I_{o2}$, as indicated in block 58. The reference values $I_{o1}$ and $I_{o2}$ are used to calibrate the system and to measure the contaminant levels on surface 30, as described below.

After determining the base reference values $I_{o1}$ and $I_{o2}$, the testing setup 20 is calibrated, as indicated in block 52, to determine a relationship between an absorbance difference and a quantity of contaminant on a surface. The first step in calibrating the testing setup 20 is to direct the infrared transmission beam 24 onto a calibration standard having a known quantity of a contaminant, as indicated in block 62. Reflected beam 34 reflected off the calibration standard passes through dual channel filter 36 wherein reflected beam 34 is filtered to pass reflected beam 34 at the first and second wavelengths $\lambda_1$ and $\lambda_2$ to dual channel infrared detector 38. The value of the infrared energy of filtered reflected beam 34 at first and second wavelengths $\lambda_1$ and $\lambda_2$ is saved as calibration values $I_{t1}$ and $I_{t2}$, as shown at block 64. The calibration values $I_{t1}$ and $I_{t2}$ along with the reference values $I_{o1}$ and $I_{o2}$, determined above, are used to calculate calibration absorbance values $A_{t1}$ and $A_{t2}$, as indicated in block 66. The calibration absorbance values $A_{t1}$ and $A_{t2}$ of the calibration standard having the contaminant of a known quantity are calculated using the equations:

$$A_{t1} = -\log_{10}\left(\frac{I_{t1}}{I_{o1}}\right) \quad \text{and} \quad A_{t2} = -\log_{10}\left(\frac{I_{t2}}{I_{o2}}\right)$$

An absorbance difference of $A_{t1}$ and $A_{t2}$ is calculated at block 68. The calibration absorbance difference and the known quantity of contaminant are then saved in a database at block 70.

As shown in block 72, the calibration steps shown in blocks 62, 64, 66, 68 and 70 are repeated, as desired, with other calibration standards having different known quantities of the contaminant to develop sufficient data points of absorbance difference and the known quantity of contaminant to determine a relationship between the absorbance difference and the quantity of the contaminant. The relationship between the absorbance difference and the quantity of the contaminant is used to determine a calibration for the quantity of the contaminate by doing a plot or linear regression of the contaminant amount values versus the absorbance differences. This calibration is then used to calculate contaminant amount directly from absorbance differences for the contaminant layer 28 on surface 30, as described in more detail below.

The compilation and calculations are suitably performed in a number of acceptable manners. For example, in one embodiment, it is performed by a processor or microprocessor (not shown) arranged to perform mathematical operations. Any processor known in the art is acceptable, such as without limitation, a Pentium®-series processor available from Intel Corp. or the like. The processor is suitably included within the infrared spectrometer or is suitably provided as a stand-alone unit that is electrically connected to receive data from the dual channel infrared detector 38. Alternatively, the calculation is performed by an electronic computer chip or is performed manually. The result of the calculations yield the calibration absorbance values $A_{r1}$ and $A_{r2}$ that correspond to a contaminant amount at block 70.

As stated above with reference to block 72, the calibration absorbance measurements can be repeated for several calibration standards with differing amounts of contaminants that are made as standards for the particular surface 30 and contaminant to be tested. These calibration standards have different quantities of the contaminant and can be made by precisely weighing a contaminate free sample of surface 30, applying a contaminant to the sample and weighing the sample with the contaminant. The difference in weight between the sample with and without the contaminant is the amount of contaminant on the sample. The amount in mg/ft$^2$ is calculated for each sample and can then be used as a calibration standard. The calibration standards, as mentioned above in relation to the reference standard, preferably have a surface finish that is similar to the surface 30 to be tested.

Figure 4A:
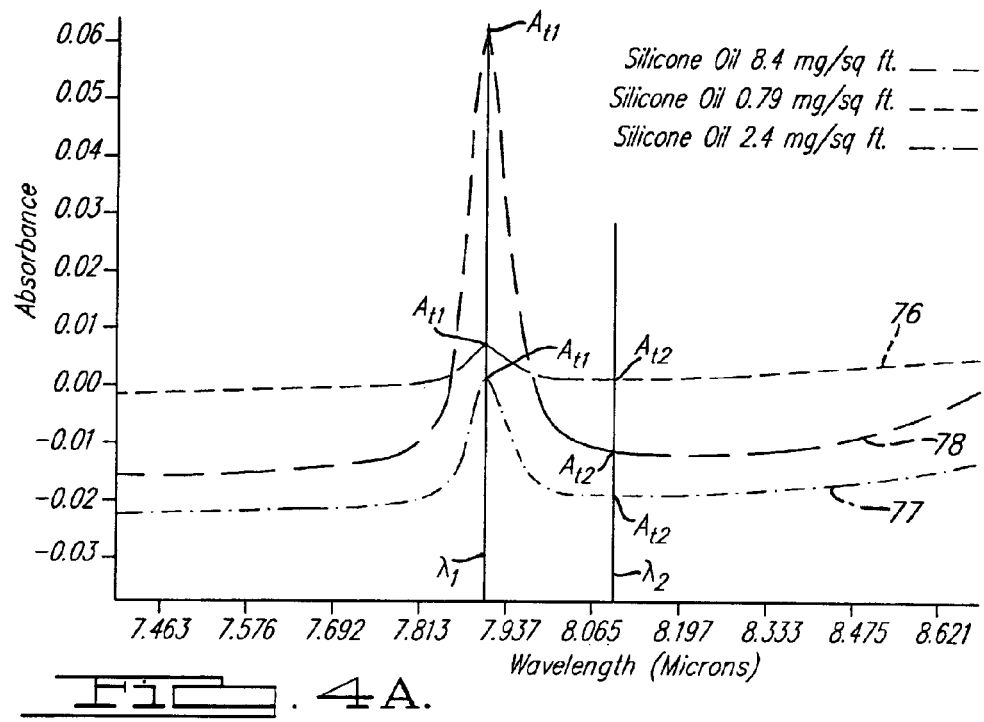
FIG. 4A is a graph of infrared absorbance for various quantities of silicone oil using the testing setup of FIG. 1.

As stated above, the absorbance of infrared energy is measured at two different wavelengths $\lambda_1$ and $\lambda_2$. The use of two different wavelengths $\lambda_1$ and $\lambda_2$ is advantageous because the absorbance values for the contaminants are small and, as such, susceptible to minor variations that can cause significant differences in the measurement of the amount of contaminant. To compensate for the potential variability the present invention utilizes a difference of absorbance at the two different wavelengths $\lambda_1$ and $\lambda_2$. The first wavelength $\lambda_1$ is chosen from a first range of wavelengths wherein the particular contaminant exhibits a peak or spike in the absorbance of infrared energy. The second wavelength $\lambda_2$ is chosen from a second wavelength range that corresponds to a range wherein the contaminant does not experience a spike or peak in absorbance of infrared energy. The second wavelength range is also chosen to include a "dead band" wherein no other contaminants that are expected to be on surface 30 cause peaks or spikes in absorbance of infrared energy. Within the second wavelength range, it is preferred that the second wavelength $\lambda_2$ be chosen to be close to the first wavelength $\lambda_1$. By having the second wavelength $\lambda_2$ close to the first wavelength $\lambda_1$, changes in the baseline absorbance (absorbance outside the first wavelength range) of infrared energy by the contaminant is minimized. That is, as can be seen in FIG. 4A, the absorbance of the curves of the various contaminant amounts outside the first wavelength range have slopes that change as the wavelength changes. By maintaining the second wavelength $\lambda_2$ in the dead band range and close to the first wavelength $\lambda_1$, the changes in the slopes of the baseline absorbance can be minimized (or corrected). This is particularly important for measurement of low level contamination where baseline slope and peak absorbance are similar.

As stated above, the first and second wavelength ranges and the respective first and second wavelengths $\lambda_1$ and $\lambda_2$ will vary depending upon the particular contaminant that is to be measured. When silicone oil is the contaminant that is to be measured, the first wavelength $\lambda_1$ is chosen from a first wavelength range that extends from about 7.85 microns to about 7.96 microns inclusive. Preferably, the first wavelength $\lambda_1$ is about 7.9 microns and most preferably about 7.91 microns. The second wavelength $\lambda_2$ is chosen from a second wavelength range that extends from about 8.05 microns to about 8.20 microns inclusive. Preferably, the second wavelength $\lambda_2$ is about 8.1 microns and most preferably about 8.10 microns.

When hydrocarbon oil or cutting oil is the contaminate to be measured, the first wavelength $\lambda_1$ is chosen from a first wavelength range that extends from about 3.36 microns to about 3.52 microns inclusive. Preferably, the first wavelength $\lambda_1$ is about 3.4 microns and more preferably about 3.42 microns. The second wavelength $\lambda_2$ is chosen from a second wavelength range that extends from about 3.60 microns to about 3.80 microns inclusive. Preferably, second wavelength $\lambda_2$ is about 3.6 microns and most preferably about 3.64 microns.

When synthetic oil or TPC residue is the contaminant to be measured, the first wavelength $\lambda_1$ is chosen from a first wavelength range that extends from about 5.65 microns to about 5.83 microns. Preferably, the first wavelength $\lambda_1$ is about 5.7 microns and most preferably about 5.73 microns. The second wavelength $\lambda_2$ is chosen from a second wavelength range that extends from about 5.40 microns to about 5.60 microns inclusive. Preferably, the second wavelength $\lambda_2$ is about 5.5 microns and most preferably about 5.52 microns.

When aqueous cleaner or long chain alcohol is the contaminant to be measured, the first wavelength $\lambda_1$ is chosen from a first wavelength range that extends from about 2.84 microns to about 3.04 microns inclusive. Preferably, the first wavelength $\lambda_1$ is about 2.9 microns and most preferably about 2.94 microns. The second wavelength $\lambda_2$ is chosen from a second wavelength range that extends from about 2.54 microns to about 2.70 microns inclusive. Preferably, the second wavelength $\lambda_2$ is about 2.6 microns and most preferably about 2.62 microns.

When a fluorocarbon is the contaminant to be measured, the first wavelength $\lambda_1$ is chosen from a first wavelength range that extends from about 8.60 microns to about 9.02 microns inclusive. Preferably, the first wavelength $\lambda_1$ is about 8.8 microns and most preferably about 8.81 microns. The second wavelength $\lambda_2$ is chosen from a second wavelength range that extends from about 9.20 microns to about 9.30 microns inclusive. Preferably, the second wavelength $\lambda_2$ is about 9.2 microns and most preferably about 9.25 microns.

FIGS. 4A and B, 5A and B, and 6A and B depict the results of performing the reference value determining portion and calibration determining portion of process 50 for silicone oil, hydrocarbon oil, and synthetic lube oil respectively. Referring to FIG. 4A, a graph of absorbance as a function of wavelength for three calibration standards having differing amounts of silicone oil are shown. The base reference values $I_{o1}$ and $I_{o2}$ and the calibration values $I_{r1}$ and $I_{r2}$ for the silicone oil are measured at a first wavelength $\lambda_1$ of 7.91 microns and a second wavelength $\lambda_2$ of 8.10 microns respectively. For each calibration standard, the calibration values $I_{r1}$ and $I_{r2}$ along with the base reference values $I_{o1}$ and $I_{o2}$ are used to calculate the absorbance values $A_{r1}$ and $A_{r2}$. Curves 76, 77, and 78 represent the calculated absorbance values of reflected beam 34 when reflected off calibration standards having 0.79 mg/ft², 2.4 mg/ft² and 8.4 mg/ft² of silicone oil contaminate respectively. The calculated absorbance values of curves 76, 77 and 78 at the first and second wavelengths $\lambda_1$ and $\lambda_2$ provide calibration absorbance values $A_{r1}$ and $A_{r2}$ for each of the respective calibration standards. The difference between the absorbance values $A_{r1}$ and $A_{r2}$ for each of the different calibration standards is determined and each results in a data point that can be used to determine the relationship between the absorbance difference and the quantity of the contaminant.

Figure 4B:
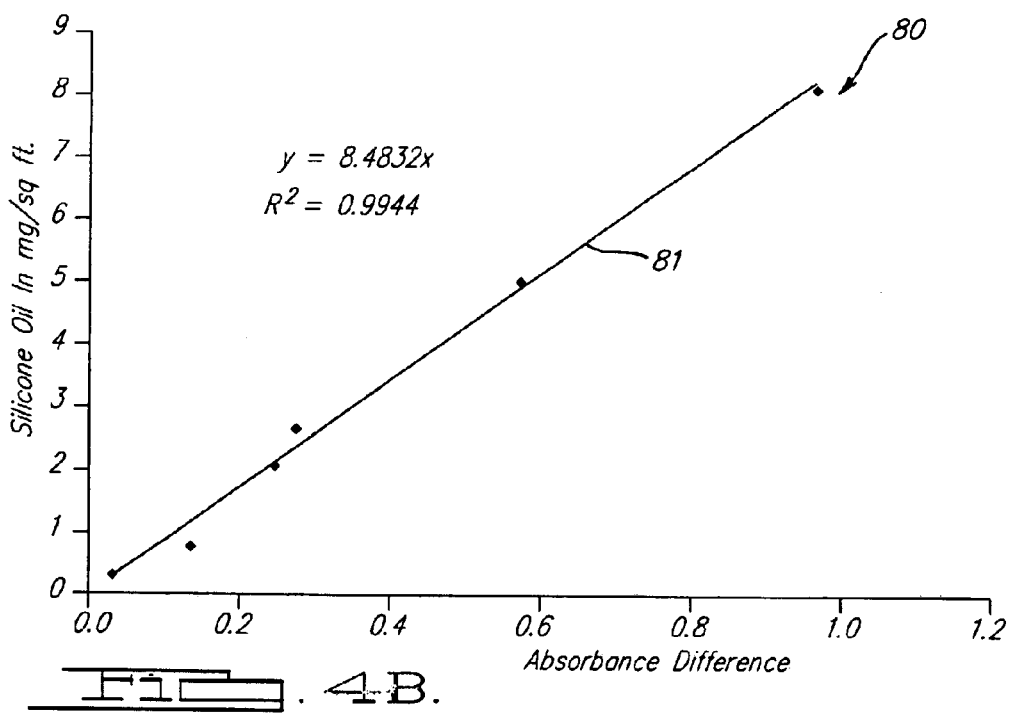
FIG. 4B is a graphical illustration of the relation between silicone oil contaminant amount and infrared absorbance difference in accordance with the present invention.

Referring now to FIG. 4B, the data points generated in FIG. 4A are plotted in graph 80 along with additional data points that were generated by different calibration standards that are not shown in FIG. 4A. The results of the calibration testing yield a curve 81 that illustrates the substantially linear relationship between the silicone oil contaminant amount and the infrared absorbance difference for infrared energy absorbed at the first and second wavelengths $\lambda_1$ and $\lambda_2$. The calibration in curve 81 can then be used to determine an amount of silicone oil contaminant on a surface 30 as described below.

The data shown in FIGS. 4A and 4B were taken with a Thermo Nicolet fourier transform infrared (FT-IR) spectrometer with a Harrick Refractor grazing angle accessory that has a reflection angle of 75 degrees. The measurement spot size is approximately 1 inch by ½ inch oval.

Figure 5A:
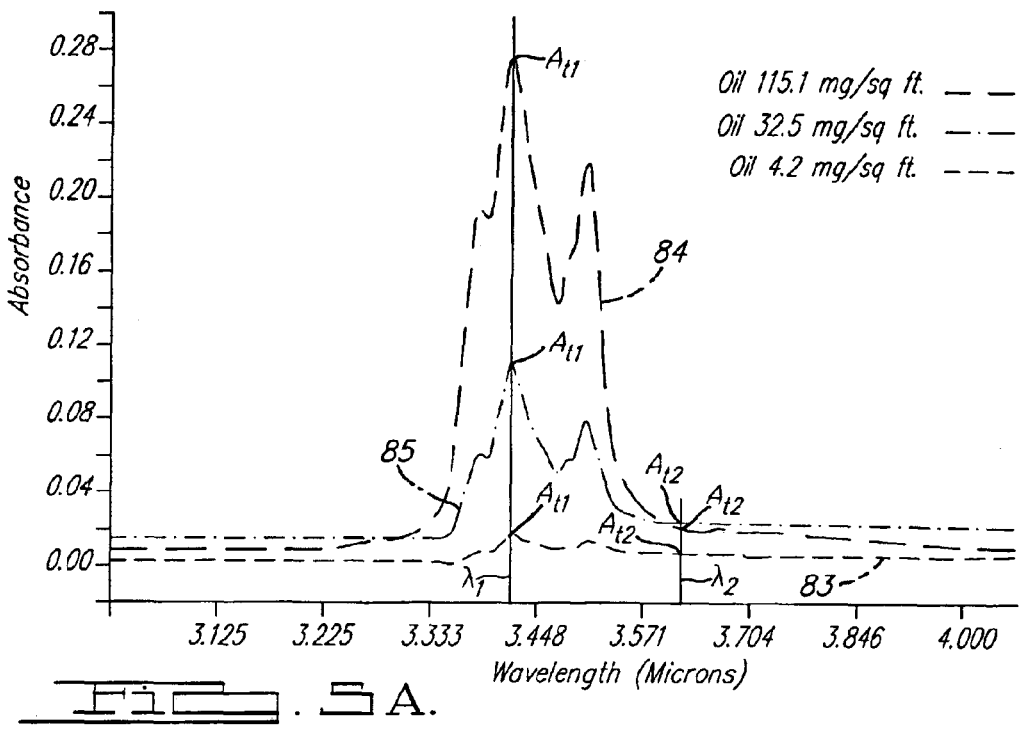
FIG. 5A is a graph of infrared absorbance for various quantities of hydrocarbon oil using the testing setup of FIG. 1.

Referring to FIG. 5A, a graph of absorbance as a function of wavelength for three calibration standards having differing amounts of hydrocarbon oil are shown. The base reference values $I_{o1}$ and $I_{o2}$ and the calibration values $I_{r1}$ and $I_{r2}$ for the hydrocarbon oil are measured at a first wavelength $\lambda_1$ of 3.42 microns and a second wavelength $\lambda_2$ of 3.64 microns respectively. For each calibration standard, the calibration values $I_{r1}$ and $I_{r2}$ along with the base reference values $I_{o1}$ and $I_{o2}$ are used to calculate the absorbance values $A_{r1}$ and $A_{r2}$. Curves 83, 84, and 85 represent the calculated absorbance values of reflected beam 34 when reflected off calibration standards having 4.2 mg/ft², 32.5 mg/ft² and 115.1 mg/ft² of hydrocarbon oil contaminant respectively. The calculated absorbance values of curves 83, 84, and 85 at the first and second wavelengths $\lambda_1$ and $\lambda_2$ provide calibration absorbance values $A_{r1}$ and $A_{r2}$ for each of the respective calibration standards. The difference between the absorbance values $A_{r1}$ and $A_{r2}$ for each of the different calibration standards is determined and each results in a data point that can be used to determine the relationship between the absorbance difference and the quantity of the contaminant.

Figure 5B:
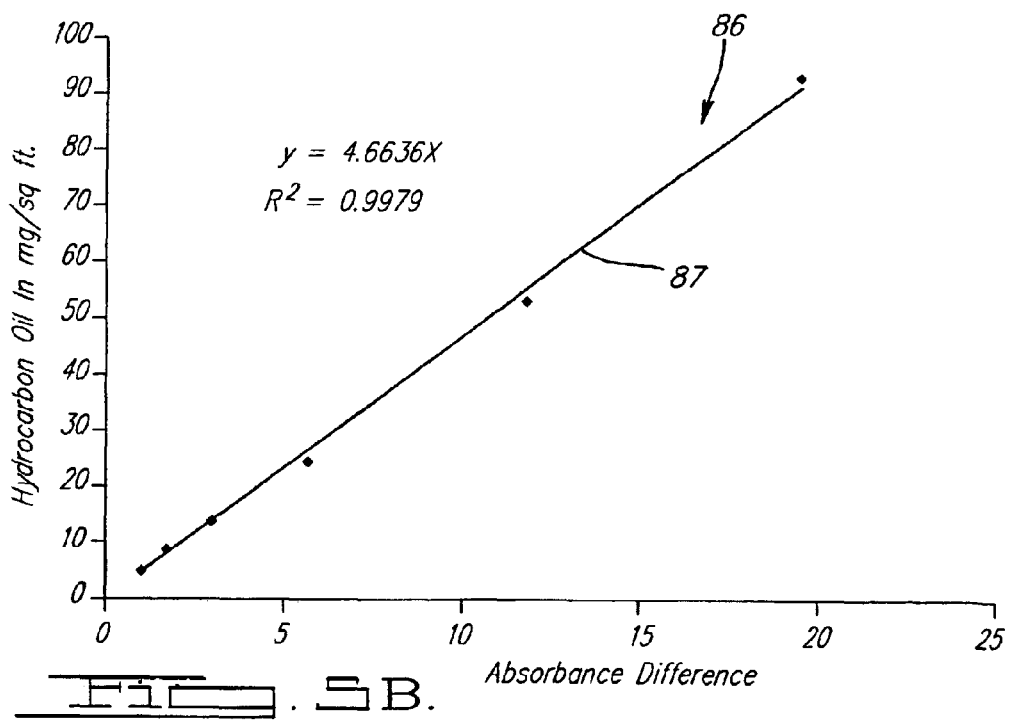
FIG. 5B is a graphical illustration of the relation between hydrocarbon oil amount and infrared absorbance difference in accordance with the present invention.
Figure 8A:
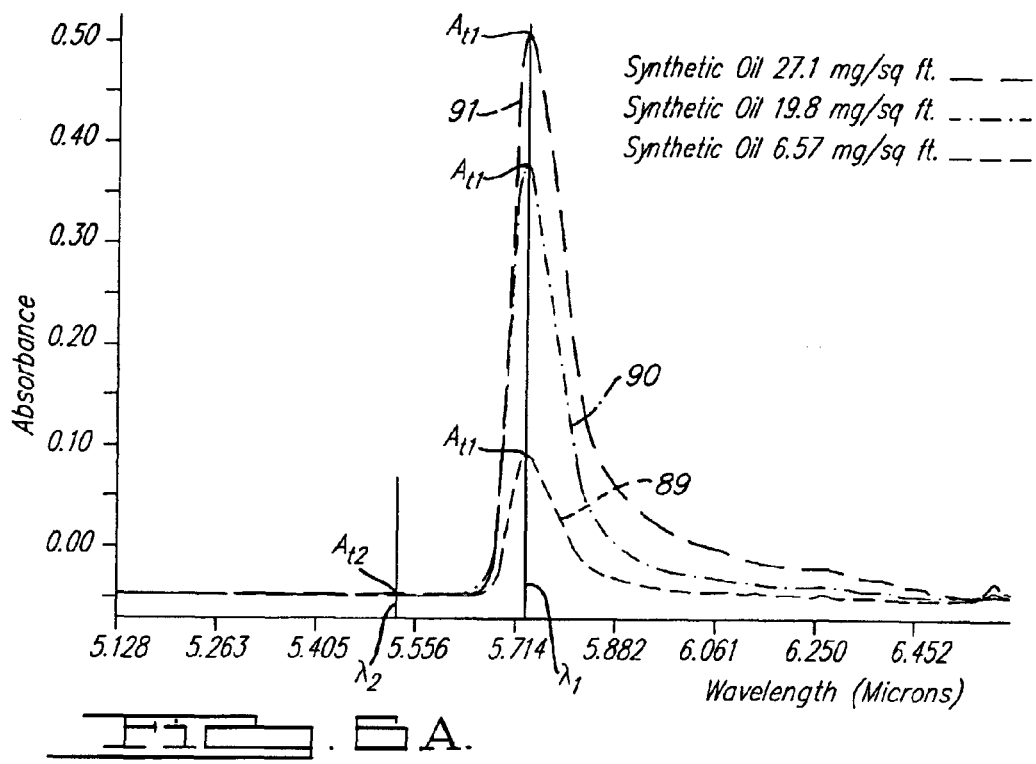
Figure 8B:
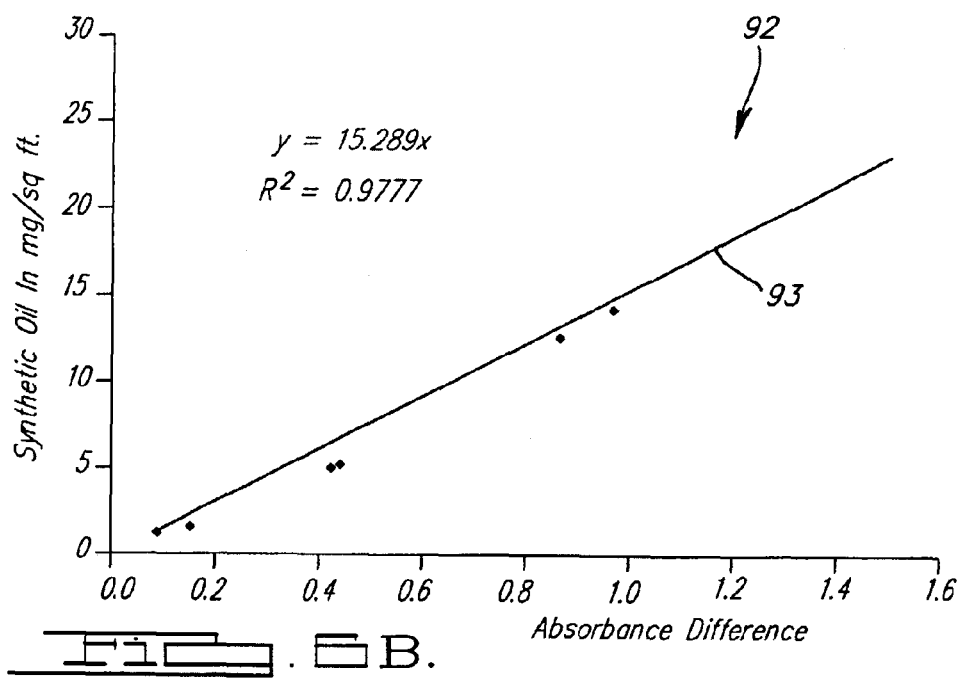

Referring now to FIG. 5B, the data points generated in FIG. 5A are plotted in a graph 86 along with additional data points that were generated by different calibration standards that are not shown in FIG. 5A. The results of the calibration testing yield a curve 87 that illustrates the substantially linear relationship between the hydrocarbon oil contaminant amount and the infrared absorbance difference for infrared energy absorbed at the first and second wave lengths $\lambda_1$ and $\lambda_2$. The calibration in curve 87 can then be used to determine an amount of hydrocarbon oil contaminant on a surface 80 as described below.

The data shown in FIGS. 5A and 5B were taken with a Thermo Nicolet model 760 spectrometer with a Harrick Refractor® reflection accessory that has a reflection angle of 75°. The measurement spot size is approximately 12.5 mm by 25 mm oval.

Referring to FIG. 6A, a graph of absorbance as a function of wavelength for three calibration standards having differing amounts of synthetic lube oil are shown. The base reference values $I_{o1}$ and $I_{o2}$ and the calibration values $I_{r1}$ and $I_{r2}$ for the synthetic oil are measured at a first wave length $\lambda_1$ of 5.73 microns and second wavelength $\lambda_2$ of 5.52 microns respectively. For each calibration standard, the calibration values $I_{r1}$ and $It_2$ along with the base reference values $I_{o1}$ and $I_{o2}$ are used to calculate the absorbance values $A_{r1}$ and $A_{r2}$. Curves 89, 90, and 91 represent the calculated absorbance values of reflected beam 34 when reflected off calibration standards having 6.57 mg/ft², 19.8 mg/ft² and 27.1 mg/ft² of synthetic oil contaminant respectively. The calculated absorbance values of curves 89, 90, and 91 at the first and second wavelengths $\lambda_1$ and $\lambda_2$ provide calibration absorbance values $A_{r1}$ and $A_{r2}$ for each of the respective calibration standards. The difference between the absorbance values $A_{r1}$ and $A_{r2}$ for each of the different calibration standards is determined and each results in a data point that can be used to determine the relationship between the absorbance difference and the quantity of the contaminant.

Referring to FIG. 6B, the data points generated in FIG. 6A are plotted in graph 92 along with additional data points that were generated by different calibration standards that are not shown in FIG. 6A. The results of the calibration testing yield a curve 93 that illustrates a substantially linear relationship between the synthetic oil contaminant amount and the infrared absorbance difference for infrared energy absorbed at the first and second wavelengths $\lambda_1$ and $\lambda_2$. The calibration in curve 93 can then be used to determine an amount of synthetic oil contaminant on a surface 30 as described below.

The data shown in FIGS. 6A and 6B, were taken with a Surface Optics Corp. FT-IR model SOC400 with a grazing angle reflectance head that uses a 75 degree reflection angle. The four curves 88, 89, 90, and 91 are all forced to a zero baseline by software that comes with the spectrometer system. The measurement spot size is approximately 1 inch by ⅓ inch oval.

It will be appreciated that FIGS. 4B, 5B and 6B represent experimental calibration data generated for different contaminants. The calibration relationship between absorbance difference and quantity of the contaminant will differ with different contaminants. As such, the infrared system that is used to measure a contaminant layer 28 on surface 30 will be calibrated for the specific contaminant for which the infrared system will be used to measure. It should further be understood that the components and operational characteristics of different infrared systems will vary from one another. As such, obtaining reference values $I_{o1}$ and $I_{o2}$, as indicated in block 51, and obtaining calibration data, as indicated in block 52, will need to be performed for each different infrared system that is to be used to measure a contaminant layer 28 on surface 30.

After performing process 50 and obtaining the reference values $I_{o1}$ and $I_{o2}$, at block 51, and the relationship between contaminant amount and absorbance difference, at block 52, the infrared system is ready to begin the measurement process 94, as shown in FIG. 3, to measure a contaminant amount on a surface. Measurement process 90 includes a contaminant infrared energy value determining portion, as indicated in block 96, and a contaminant amount determining portion, as indicated in block 98. To determine the contaminant infrared energy, infrared transmission beam 34 is transmitted through a contaminant layer 28 on surface 30, as indicated in block 100. Reflected beam 34 reflects off surface 30 and passes through dual channel filter 36 and onto dual channel infrared detector 38, as indicated in block 102. The detected energy levels at first and second wavelengths $\lambda_1$ and $\lambda_2$ are saved as $I_{c1}$ and $I_{c2}$.

After obtaining the values $I_{c1}$ and $I_{c2}$, the amount of contaminant is determined, as indicated in block 98. Using the references values $I_{o1}$ and $I_{o2}$, determined in block 51 of process 50, and the contaminant values $I_{c1}$ and $I_{c2}$, the absorbance of the contaminant layer 28 is calculated using the equations:

$$A_1 = -\log_{10}\left(\frac{I_{c1}}{I_{o1}}\right) \quad \text{and} \quad A_2 = -\log_{10}\left(\frac{I_{c2}}{I_{o2}}\right)$$

as indicated in block 104. After determining the absorbance values $A_1$ and $A_2$, a difference of the absorbance values is determined, as indicated in block 106. The difference is then correlated, at block 108, with the contaminant amount using the relationship (calibration curve) determined when calibrating the infrared system for the specific contaminant being measured. Finally, based on the correlation, the contaminant amount is generated, as indicated in block 110.

It will be appreciated that parameters such as incident beam angle $\alpha$, size of spot 32, and overall incident beam path length are maintained substantially similar when determining the reference values, the calibration data, and the contaminant infrared energy values.

Thus, the present invention provides a method of determining a quantity of a contaminant on a surface using infrared spectroscopy. While specific examples have been shown to illustrate the use of the method to determine a quantity of a specific contaminant on a surface, it should be understood that the method can also be used for the other contaminants listed above using the respective first and second wavelength ranges disclosed.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of determining an amount of a contaminate on a surface, the method comprising the steps of:
    (a) determining a difference of first and second absorbance values $A_1$ and $A_2$ of infrared energy absorbed in a contaminate on a surface at respective first and second wavelengths, said second wavelength being different than said first wavelength; and
    (b) correlating said difference to an amount of said contaminate on said surface.

2. The method of claim 1, wherein said contaminate includes at least one of silicone oil, hydrocarbon oil, synthetic oil, TPC residue, aqueous cleaner, cutting oil, long chain alcohol and fluorocarbon.

3. The method of claim 1, wherein said first wavelength is about 7.9 microns and said second wavelength is about 8.1 microns.

4. The method of claim 1, wherein said first wavelength is about 3.4 microns and said second wavelength is about 3.6 microns.

5. The method of claim 1, wherein said first wavelength is about 5.7 microns and said second wavelength is about 5.5 microns.

6. The method of claim 1, wherein said first wavelength is about 2.9 microns and said second wavelength is about 2.6 microns.

7. The method of claim 1, wherein said first wavelength is about 8.8 microns and said second wavelength is about 9.2 microns.

8. The method of claim 1, wherein step (a) further comprises determining first and second reference values $I_{o1}$ and $I_{o2}$ of infrared energy reflected at said first and second wavelengths respectively from a standard having a quantity of said contaminate below a predetermined value.

9. The method of claim 8, wherein step (a) further comprises determining first and second contaminate values $I_{c1}$ and $I_{c2}$ of infrared energy reflected at said first and second wavelengths respectively from said surface having said contaminate.

10. The method of claim 9, wherein said first and second absorbance values $A_1$ and $A_2$ are calculated according to the equations $$A_1 = -\log_{10}(I_{c1}/I_{o1}) \text{ and } A_2 = -\log_{10}(I_{c2}/I_{o2}).$$

11. The method of claim 8, wherein said predetermined value is less than about 0.01 mg/ft$^2$.

12. The method of claim 1, wherein said surface has a refractive index of greater than about 3.

13. The method of claim 1, wherein said surface includes one of aluminum, aluminum alloy, titanium and titanium alloy.

14. A method of determining an amount of a contaminate on a surface comprising the steps of:
    (a) transmitting an infrared beam through a contaminate on a surface at a predetermined incident beam angle relative to normal, said transmitted beam having a cross-sectional area to produce a predetermined spot size on said surface;
    (b) reflecting said infrared beam off said surface to form a reflected beam;
    (c) detecting said reflected beam;
    (d) comparing infrared energies $I_{c1}$ and $I_{c2}$ of said reflected beam at respective first and second wavelengths, said first wavelength being different than said second wavelength, with predetermined values of infrared energies $I_{o1}$ and $I_{o2}$ at said respective first and second wavelengths reflected off a standard having a quantity of said contaminate below a predetermined value to determine absorbance values $A_1$ and $A_2$ at said respective first and second wavelengths for said surface having said contaminate;
    (e) determining a difference of said absorbance values $A_1$ and $A_2$; and
    (f) correlating said difference to an amount of said contaminate on said surface.

15. The method of claim 14, wherein said predetermined spot size is in a range from about 2 mm to about 35 mm in diameter.

16. The method of claim 15, wherein said predetermined spot size is an oval of about 12.5 mm by about 25 mm.

17. The method of claim 14, wherein said predetermined incident beam angle is in a range from about 70 degrees to about 80 degrees from normal.

18. The method of claim 17, wherein said predetermined incident beam angle is about 75 degrees from normal.

19. The method of claim 14, wherein said surface includes one of aluminum, aluminum alloy, titanium and titanium alloy.

20. The method of claim 14, wherein step (c) is performed with an infrared imaging system.

21. The method of claim 14, wherein step (c) is performed with a broadband infrared spectrometer system.

22. The method of claim 14, wherein step (c) is performed with an infrared bandpass filter system.

23. The method of claim 14, wherein said first and second absorbance values $A_1$ and $A_2$ are calculated according to the equations $$A_1 = -\log_{10}(I_{c1}/I_{o1}) \text{ and } A_2 = -\log_{10}(I_{c2}/I_{o2}).$$

24. The method of claim 14, further comprising the step of filtering at least one of said infrared beam and said reflected beam to said first and second wavelengths.

25. The method of claim 14, wherein said contaminate includes at least one of silicone oil, hydrocarbon oil, synthetic oil, TPC residue, aqueous cleaner, cutting oil, long chain alcohol and fluorocarbon.

26. The method of claim 14, wherein said first wavelength is about 7.9 microns and said second wavelength is about 8.1 microns.

27. The method of claim 14, wherein said first wavelength is about 3.4 microns and said second wavelength is about 3.6 microns.

28. The method of claim 14, wherein said first wavelength is about 5.7 microns and said second wavelength is about 5.5 microns.

29. The method of claim 14, wherein said first wavelength is about 2.9 microns and said second wavelength is about 2.6 microns.

30. The method of claim 14, wherein said first wavelength is about 8.8 microns and said second wavelength is about 9.2 microns.

31. A method of determining an amount of a contaminate on a surface, the method comprising the steps of:

(a) transmitting an infrared beam having a predetermined wavelength within a range of about 2.5 microns to about 25 microns through a contaminate on a surface at a predetermined incident beam angle in a range from about 70 degrees to about 80 degrees from normal, said transmitted beam having a cross-sectional area to produce a predetermined spot size on said surface;

(b) reflecting said infrared beam off said surface to form a reflected beam;

(c) detecting said reflected beam;

(d) comparing infrared energies $I_{c1}$ and $I_{c2}$ of said reflected beam at respective first and second wavelengths, said first wavelength being different than said second wavelength, with predetermined values of infrared energies $I_{o1}$ and $I_{o2}$ at said respective first and second wavelengths reflected off a standard having a quantity of said contaminate below a predetermined value to determine absorbance values $A_1$ and $A_2$ at said respective first and second wavelengths for said contaminate;

(e) determining a difference of said absorbance values $A_1$ and $A_2$; and (f) correlating said difference to an amount of said contaminate on said surface.

32. The method of claim 31, wherein said predetermined spot size is in a range from about 2 mm to about 35 mm in diameter.

33. The method of claim 31, wherein said predetermined spot size is an oval of about 12.5 mm by about 25 mm.

34. The method of claim 31, wherein said surface includes one of aluminum, aluminum alloy, titanium and titanium alloy.

35. The method of claim 31, wherein said first and second absorbance values $A_1$ and $A_2$ are calculated according to the equations $$A_1 = -\log_{10}(I_{c1}/I_{o1}) \text{ and } A_2 = -\log_{10}(I_{c2}/I_{o2}).$$

36. The method of claim 31, further comprising the step of filtering at least one of said infrared beam and said reflected beam to said first and second wavelengths.

37. The method of claim 31, wherein said contaminate includes at least one of silicone oil, hydrocarbon oil, synthetic oil, TPC residue, aqueous cleaner, cutting oil, long chain alcohol and fluorocarbon.

38. The method of claim 31, wherein said first wavelength is about 7.9 microns and said second wavelength is about 8.1 microns.

39. The method of claim 31, wherein said first wavelength is about 3.4 microns and said second wavelength is about 3.6 microns.

40. The method of claim 31, wherein said first wavelength is about 5.7 microns and said second wavelength is about 5.5 microns.

41. The method of claim 31, wherein said first wavelength is about 2.9 microns and said second wavelength is about 2.6 microns.

42. The method of claim 31, wherein said first wavelength is about 8.8 microns and said second wavelength is about 9.2 microns.

* * * * *